United States Patent [19]

Mössle et al.

[11] Patent Number: 4,578,033
[45] Date of Patent: Mar. 25, 1986

[54] TARTAR-REMOVING DENTAL HANDPIECE

[75] Inventors: Walter Mössle, Bad Waldsee; Eugen Eibofner, Biberach, both of Fed. Rep. of Germany

[73] Assignee: Kaltenbach & Voight GmbH & Co., Biberach, Fed. Rep. of Germany

[21] Appl. No.: 634,784

[22] Filed: Jul. 26, 1984

[30] Foreign Application Priority Data

Aug. 8, 1983 [DE] Fed. Rep. of Germany ....... 3328604

[51] Int. Cl.⁴ .............................................. A61C 3/00
[52] U.S. Cl. ..................... 433/29; 433/118; 433/120; 433/126
[58] Field of Search ............... 433/29, 119, 118, 120, 433/126

[56] References Cited

U.S. PATENT DOCUMENTS

| 2,038,911 | 4/1936 | Stutz et al. | 433/29 |
| 3,109,238 | 11/1963 | Marks | 433/29 |
| 3,930,173 | 12/1975 | Banko | 433/119 |
| 4,341,518 | 7/1982 | Wallace | 433/29 |
| 4,398,885 | 8/1983 | Loge et al. | 433/29 |
| 4,460,337 | 7/1984 | Landgraf et al. | 433/29 |
| 4,484,893 | 11/1984 | Finn | 433/29 |

FOREIGN PATENT DOCUMENTS 1349227 4/1974 United Kingdom ............... 433/29

Primary Examiner—John J. Wilson
Attorney, Agent, or Firm—Scully, Scott, Murphy & Presser

[57] ABSTRACT

A tartar-removing dental handpiece, constituted of an elongated gripping sleeve having a vibration generator arranged therein which is connected with a vibratable tartar-removing instrument located at one end of the gripping sleeve for transmission of vibrations. The gripping sleeve includes supply media conduits of which one is an energy infeed conduit leading to the vibration generator, and which are connected through the intermediary of a coupling member, which is arranged at the end of the gripping sleeve remote from the instrument, to connecting conduits leading to a medium source.

28 Claims, 13 Drawing Figures

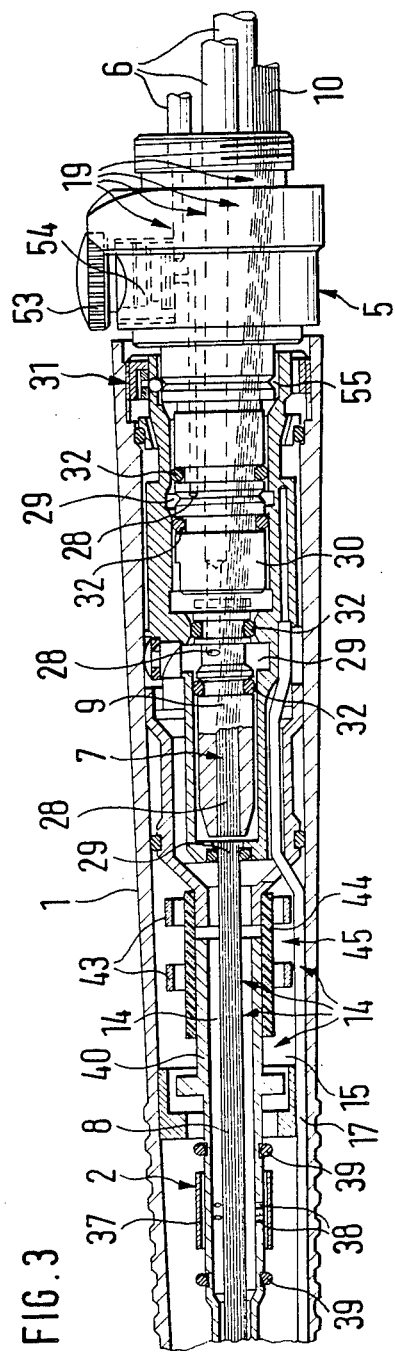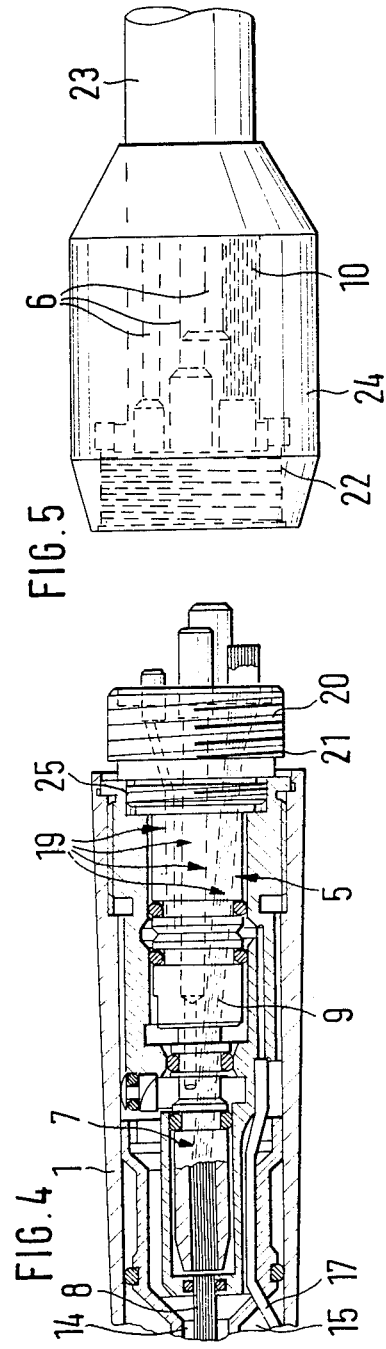

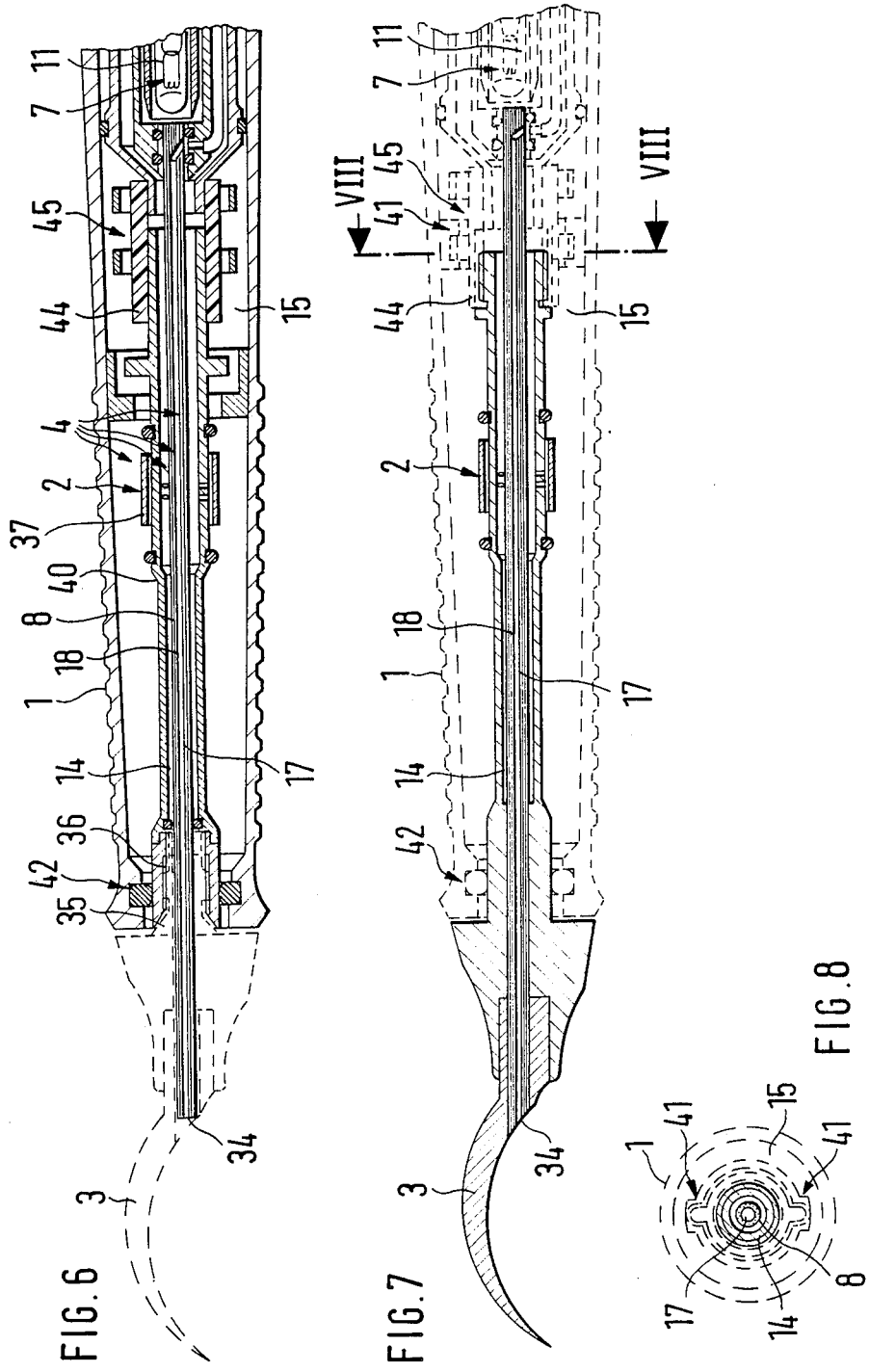

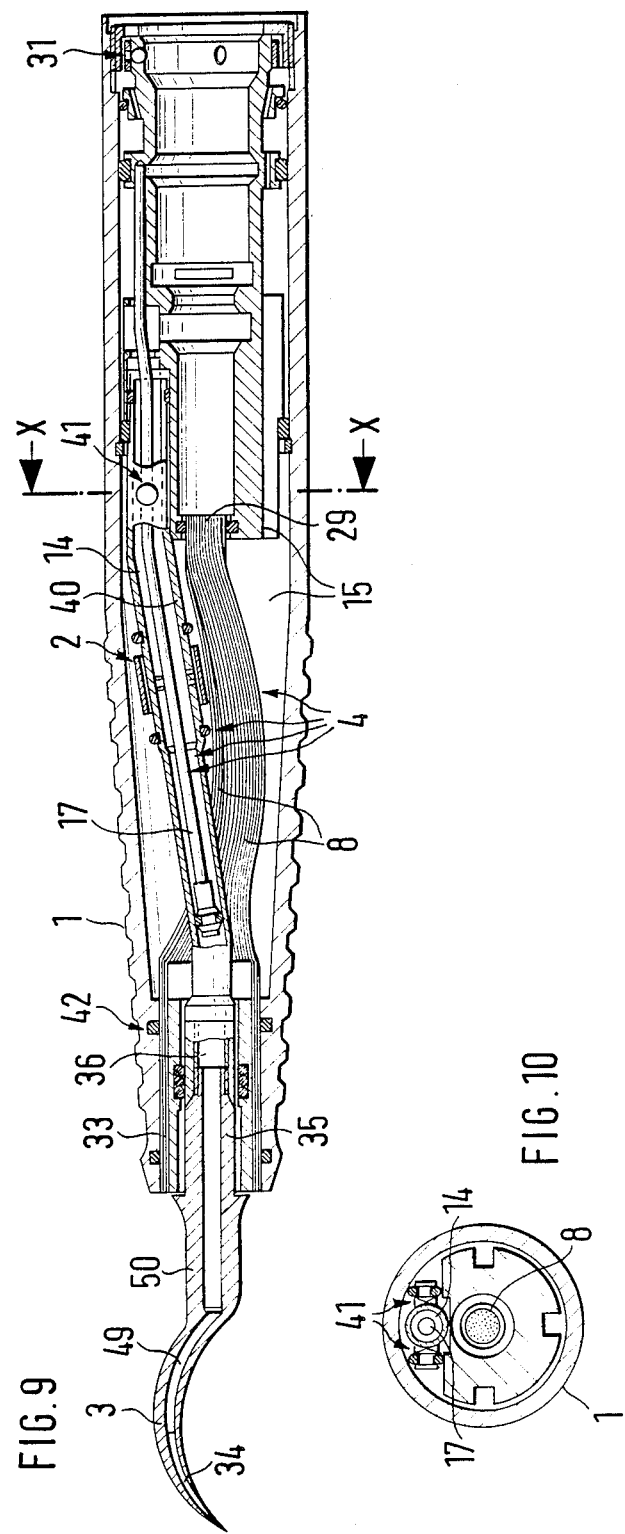

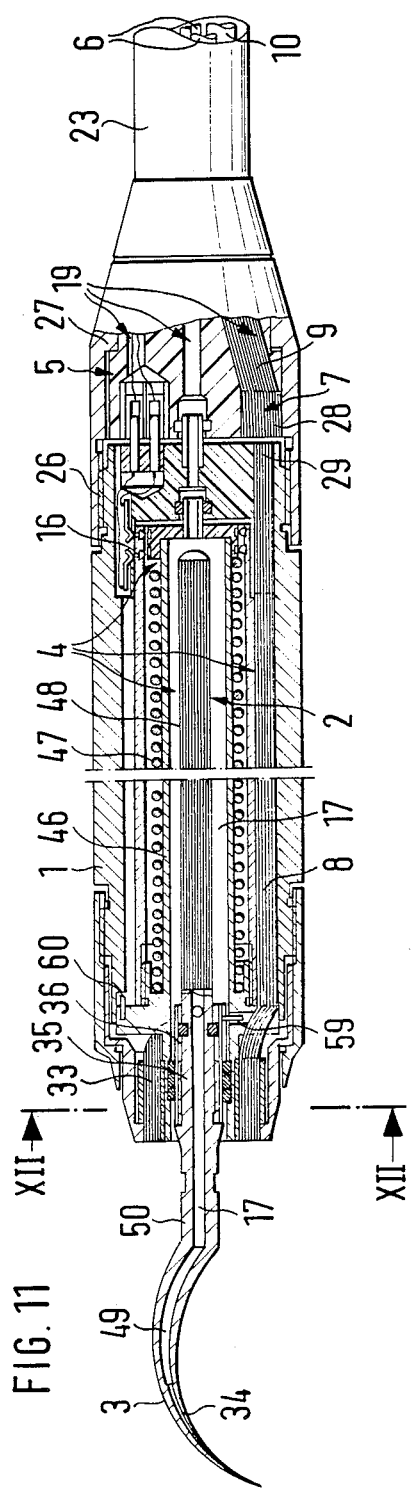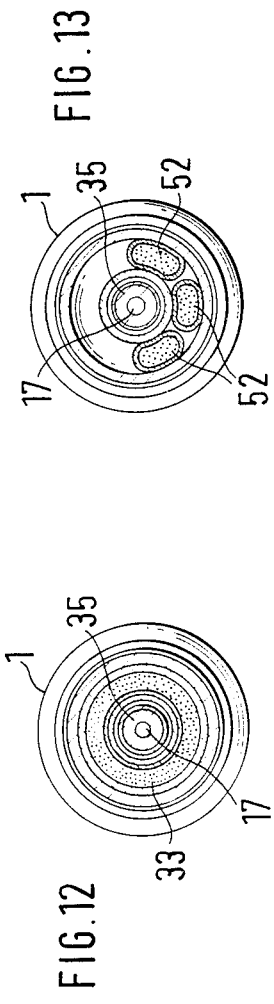
FIG. 11
FIG. 12
FIG. 13

TARTAR-REMOVING DENTAL HANDPIECE

BACKGROUND OF THE INVENTION

1. Field of the Invention

The present invention relates to a tartar-removing dental handpiece, constituted of an elongated gripping sleeve having a vibration generator arranged therein which is connected with a vibratable tartar-removing instrument located at one end of the gripping sleeve for transmission of vibrations, wherein the gripping sleeve includes supply media conduits of which one is an energy infeed conduit leading to the vibration generator, and which are connected through the intermediary of a coupling member, which is arranged at the end of the gripping sleeve remote from the instrument, to connecting conduits leading to a medium source.

2. Discussion of the Prior Art

Tartar-removing dental handpieces of that type have become known from the disclosures of European patent application No. 28531 and German AS No. 16 16 127. In these presently known tartar-removing dental handpieces it has been shown that the incidence of light on the location of the tooth of the patient which evidences the tartar, in particular when this location is at a deep or backwardly recessed tooth part or on the rear surface of the tooth, that the lighting conditions heretofore encountered in the dental practice have been inadequate.

SUMMARY OF THE INVENTION

The present invention, as can be ascertained from the detailed description set forth hereinbelow, provides for the creation of a tartar-removing dental handpiece of the above-mentioned type, in which the location of the tooth which is to be treated during tartar removal is sufficiently bright and thereby clearly recognizable to the treating person.

The advantages which are attained through the utilization of present invention can be essentially ascertained in that there is now afforded a complete illumination of the location of the tooth which is to be treated, such that the treating person can clearly follow and recognize the procedure of the tartar removal. In this manner there can be avoided that, on the one hand, because of poor recognizability there is carried out a treatment extending over an excessively lengthy time period and thereby possibly causing damage to the tooth which is already free of tartar, and on the other hand, tartar is removed to only an insufficient extent.

From the disclosure of German OS 31 04 239 there is already known a dental handpiece in which there is also provided a fiber-shaped light conductor as a supply medium conduit which has its leading end directed towards the instrument and wherein the rearward end thereof is supplied with light from a light producing element, and in which the light conductor is arranged at the end of the coupling member facing towards the instrument. However, this known handpiece belongs to an entirely different constructional class; thus, it does not pertain to a tartar-removing dental handpiece, and in the gripping sleeve no provision is made for a vibration generator for a vibratable tartar-removing instrument. In contrast, in the known handpiece, at one end of the gripping sleeve there is provided a drive assembly which is constructed as an air turbine for the direct operation of a rotatable dental treatment instrument. In such a handpiece, the illumination of the treating location has certain advantages; however, it is of subordinate significance in comparison with a tartar-removing dental handpiece, inasmuch as, subsequent to the treatment with the known air turbine handpiece, there is always carried out a follow-up treatment, for example, the insertion of a filling, whereas subsequent to the treatment with a tartar-removing dental handpiece, the treatment is completed such that any encountered damage to the tooth can no longer be repaired.

BRIEF DESCRIPTION OF THE DRAWINGS

Advantageous embodiments and features of the invention may now be ascertained by reference to the following detailed description thereof, taken in conjunction with the accompanying drawings; in which:

FIG. 3 illustrates a modified embodiment with respect to that of FIG. 1;

FIG. 4 illustrates a modified embodiment with respect to that of FIG. 3;

FIG. 5 illustrates a supply hose connectable with a coupling member for the handpiece at the end remote from the instrument in accordance with either FIGS. 1, 3 or 4;

FIG. 6 illustrates a sectional view of a further embodiment of a tartar-removing dental handpiece with the end thereof remote from the instrument having been omitted;

FIG. 7 illustrates a modified embodiment with respect to that of FIG. 6;

FIG. 8 is a sectional view taken along line VIII—VIII in FIG. 7;

FIG. 9 illustrates a modified embodiment with respect to that of FIGS. 6 and 7;

FIG. 10 illustrates a sectional view taken along line X—X in FIG. 9;

FIG. 11 illustrates a sectional view of a tartar-removing dental handpiece with an electrically operable vibration generator;

FIG. 12 illustrates a sectional view taken along line XII—XII in FIG. 11; and

FIG. 13 illustrates a modified embodiment with respect to that of FIG. 12.

DETAILED DESCRIPTION

Figures 1, 2:
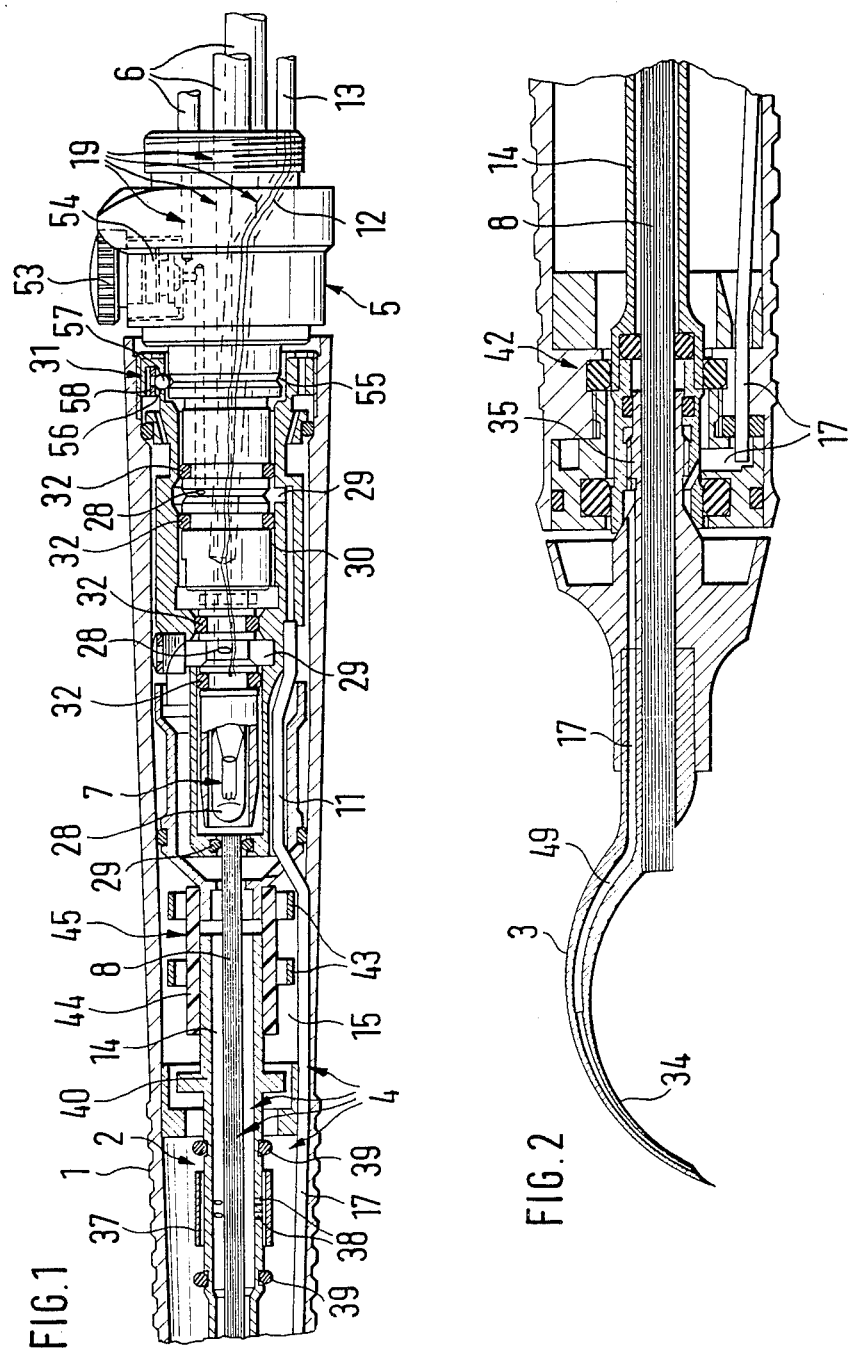
FIG. 1 illustrates a longitudinal sectional view through a tartar-removing dental handpiece with a pneumatically operable vibration generator, with the left-hand end portion of the instrument having been omitted.
FIG. 2 illustrates the left-hand end of the handpiece of FIG. 1 on an enlarged scale.

The tartar-removing dental handpiece comprises an elongated round gripping sleeve 1 having a vibration generator 2 arranged therein which, in order to set a tartar-removing instrument 3 into vibrating, wherein the implement is vibratably supported at one end of the gripping sleeve, is connected with the instrument 3 for the purpose of transmitting vibrations thereto. The gripping sleeve 1 possesses media supply conduits 4 interiorly thereof which, through the interposition of intermediate conduits 19 of a coupling member 5 which is arranged at the end of the gripping sleeve 1 remote from the instrument, are coupled to a connecting conduit 6 leading to a medium supply source (not shown).

As a further medium supply conduit 4 there is provided a light conductor 8 which has its leading end directed towards the treating or working area of the tartar-removing instrument 3, and which at its rearward end, in essence, that remote from the instrument, is supplied with light from a light supplying element 7 which is located at the end of the coupling member 5 facing towards the instrument. The light conductor 8 can consist of a bundle of optic fibers which are formed, for example, of glass, plastic material or the like.

In the embodiments pursuant to FIGS. 3, 4 and 11, the light supplying element 7 is formed by the end of an intermediate light conductor 9 extending towards the instrument and which is arranged within the coupling member 5, which is, at its end remote from the instrument suppliable with light from the end of a connecting light conductor 10 towards the instrument, which is supplied with light from a medium source formed by a light source.

The light supplying element 7 in the embodiments of FIGS. 1, 6 and 7 is formed by an incandescent lamp 11, which is associated with a current line 12 located in the coupling member 5, which line has its end remote from the instrument connectable to the end of a coupling current line 13 facing the instrument and leading to a current source as its medium source.

In the instance of FIGS. 1 through 10, the vibration generator 2 is pneumatically operable, wherein the energy inlet conduit is formed by a compressed-air conduit 14. In the embodiments according to FIGS. 1 through 8, the light conductor 8 is arranged coaxially within the compressed air conduit 14 so as to allow for the presence of an annular open space therebetween.

Provided as a further medium supply conduit 4 is an exhaust air conduit 15 which extends from the vibration generator 2, and which in the region of the vibration generator 2 is essentially formed by the internal space of the gripping sleeve 1. The vibration generator 2, in the embodiment of FIGS. 1 through 10, in the type as shown in European patent application No. 28 531, consists of a sleeve 37 which loosely encompasses the compressed-air conduit 14 so as to form a gap and is thereby radially movable, which has air blown thereagainst through radially directed bores 38 in the compressed-air conduit 14 and is thereby placed into radially reciprocating movements. The impacts which are hereby exerted against the compressed-air conduit 14 produce vibrations which, as a result of the connection with the tartar-removing instrument 3, are then transmitted to the latter. In order that the sleeve 37 will be always located in the region of the incoming air bores 38, the axial extent of reciprocating movement of the sleeve 37 is limited by annular stops 39 which are arranged on the conduit 14. The compressed-air conduit 14 which can be set into vibrations is formed in the type of a resonance member 40. Located between the compressed-air conduit 14 and the gripping sleeve 1 is a device 4 for protection against torsion, which is illustrated in FIGS. 7 through 10.

The support of the end of the compressed-air conduit 14 towards the instrument which transmits the vibrations is designated by reference numeral 42, and the end of the support remote from the instrument which incorporates a sling-type of clamping arrangement 43 for a coupling hose 44, is designated by reference numeral 45.

The embodiment pursuant to FIG. 11, the vibration generator is electrically operable, wherein the energy supply conduit is formed by a current supply conductor or line 16. The vibration generator 2 in this embodiment, similar to that disclosed in German AS No. 16 16 127, consists of a tubular support element 46 arranged coaxially with the gripping sleeve 1, on which there is arranged an energizing winding 47 which is connected with the current supply line 16. Arranged within the tubular support element 46, and coaxially with the tubular support element 46, is a magneto-strictive converter 48, which is set into vibrations during the supply of a current, and transmits these vibrations to the instrument 3 which is connected therewith. Provided as an additional medium supply conduit 4 is a cooling medium conduit 17 which leads to the tartar-removing instrument 3. The cooling medium can be air, water or a spray formed from an air-water mixture. In the embodiments pursuant to FIGS. 2 and 11, the cooling medium conduit 70 connects into the hollow-constructed instrument 3 which incorporates a cooling medium-outlet aperture 34 facing towards the treating area. The hollow passageway of the instrument 3 is designated by reference numeral 49.

In the embodiments pursuant to FIGS. 6 through 8, the light conductor 8 is constructed to be hollow, whereby the so formed hollow passageway 18 constitutes the cooling medium conduit 17, or a receiver for the cooling medium conduit.

In the instance of FIGS. 4 and 11, the coupling member 5 includes a screw thread so as to be secured against rotation with the end of the gripping sleeve 1 which is remote from the instrument. According to FIG. 4, considered in conjunction with FIG. 5, the coupling member 5 is screwed into the end of the gripping sleeve 1 which is remote from the instrument through a screw connection 25, and is provided with a projection 20 extending outwardly of this end. This projection 20, in turn, is provided with an external screw thread 21 for its screwing together with the internal screw threads 22 of a lock nut 24 which is arranged on the end of a supply hose 23 towards the gripping sleeve, and which contains the connecting conduits 6, 10, 13.

In the embodiment pursuant to FIG. 11, the threaded connection of the coupling member 5 with the gripping sleeve is effected in the manner such that the coupling member 5 is arranged at the end of a supply hose 23 towards the gripping sleeve which contains the connecting conduits 6, 10, 13, and is provided with a lock nut 27 screwable together by means of screw thread connection 26 with the end of the gripping sleeve which is remote from the instrument.

In contrast therewith, in the instance of the embodiments of FIG. 1 and 3, the coupling member 5 is rotatably connected with the gripping sleeve 1. For this purpose, the construction is such that the coupling member 5 is formed as a quick-connect coupling which is freely rotatable with respect to the gripping sleeve 1, whereby the quick-connect coupling and the end of the gripping sleeve 1 which is remote from the instrument are provided with media transfer means 28, 29 which are operative in every position of rotation. Hereby, the coupling member 5 is provided with guide trunnions 30, which are circular in cross-section, and which are insertable into the end of the gripping sleeve 1 which is distant from the instrument.

The media transfer means for liquid, air or for a spray which is formed from a liquid-air mixture, is presently formed by discharge openings 28 between two annular sealing elements 32 which encompass the guide trunnion 30 and which are in contact with the inner gripping sleeve wall, which openings 28 are in the intermediate conduits 19 of the coupling member 5 which are connected to the connecting conduits 6, and by means of annular passageways 29 associated with the discharge opening 29, and provided in the region of the gripping sleeve inner wall, and which are in communication with the media supply conduits 4.

For instance, when in accordance with FIG. 11, there is provided as a medium supply conduit 4 a current supply line 16 which leads to the vibration generator 2, then the medium transfer means can be formed, on the one hand, by ring contacts provided on the guide trunnion 30, and on the other hand, by sliding contacts of the current supply line 16 provided in the region of the gripping sleeve wall and cooperating with the ring contacts.

The media transfer means 28, 29 for light are formed by a light supplying element 7 arranged on the end of the guide trunnion 30 facing towards the instrument and by the rear end of the light conductor 8. The light conductor 8 is arranged coaxially within the gripping sleeve 1.

In the embodiments pursuant to FIGS. 9 and 11, viewed in conjunction with FIG. 12, the light conductor 8 is formed as a light conductor ring 33 which at its end towards the instrument, encompasses the shaft 50 and/or an extension 35 of the instrument. Hereby, the light conductor 8 is formed from two strands or fibers. In the case of FIG. 11, as viewed in conjunction with FIG. 13, the end of the light conductor 8 facing towards the instrument consists of individual strands which are arranged adjoining each other so as to extend along a circle. Otherwise, the light conductor 8 can be directed point-like towards the instrument 3.

In the embodiments pursuant to FIGS. 2 and 11 the free end of the light conductor 8 is arranged separately from the discharge opening 34 of the cooling medium conduit 17. In the embodiments according to FIGS. 6 and 7, in contrast therewith, the free end of the light conductor 8 is structurally combined with the discharge opening 34 for the cooling medium conduit 17.

In the embodiments pursuant to FIGS. 6 and 9, the tartar-removing instrument 3 is detachably connected with the vibration generator 2. For this purpose, the extension 35 which is provided at the end of the tartar-removing instrument 3 facing towards the gripping sleeve, is inserted into a receiving aperture 36 in the vibration generator 2. In this manner there is facilitated an easy exchange for the instrument. In the embodiment pursuant to FIGS. 6 and 7, the light conductor 8 extends axially through the extension 35 of the instrument 3; with its end directed towards the tip of the arcuately-shaped instrument 3.

In the instance of FIGS. 7 and 8, the tartar-removing instrument 3 is constructed as a preferably detachable or exchangeable unitary structure together with the vibration generator 2. The vibration generator 2 extends up to the end of the gripping sleeve 1 which is distant from the instrument.

In the embodiments according to FIGS. 1, 2, 3, 6 and 7, the light conductor 8 is arranged internally of the vibration generator 2; in effect, within the compressed-air conduit 14.

In the case of FIG. 9, the vibration generator 2 and the compressed-air conduit 13 extend positioned eccentrically; in the remaining embodiments there is provided for a centered positioning within the gripping sleeve 1.

The coupling member 5, in the embodiments of FIGS. 1 and 3, possesses at least one regulating component 54 which is provided with an externally-actuatable control element 53, and which is associated with at least the medium supply conduit 4 serving as the cooling medium conduit 17.

Insofar as, for the clamping force which is necessary for the restraint of the guide trunnion 30 within the gripping sleeve 1, the elasticity of the sealing elements 32 is insufficient, as illustrated in FIGS. 1, 3 and 9, there can therefore be provided a latching arrangement 31 which will retain the guide trunnion 30 in the required inserted axial position. For this purpose, on the outer wall of the guide trunnion 30 there is provided a special latching annular channel 55, and in the wall of the gripping sleeve 1 at least one locking ball 57 which is supported in a recess 56. Hereby, the locking ball 57 in response to the effect of a spring 58, engages into latching annular channel 55 with the smaller portion of its surface projecting beyond the inner surface of the wall of the gripping sleeve 1. For this purpose, the recess 56 possesses a bottom surface which is in alignment with the above-mentioned inner surface of the wall of the gripping sleeve 1, which possesses an opening which is smaller than the diametral plane of the locking ball 57. During the inserting or during the pulling apart procedure, the locking ball 57 is moved out of the latching annular channel 55 against the effect of the spring 58, so that during the inserting or during the pulling apart procedure there is achieved a light and rapid assumption of and release from the latched position.

In FIG. 11 there can also be ascertained, in the region of the end of the handpiece towards the instrument, a pin 59 forming a security against rotation, and a locking pin 60.

What is claimed is:

1. In a tartar-removing dental handpiece, including an elongated gripping sleeve; a vibratable tartar-removing instrument arranged at one end of said gripping sleeve; a pneumatically operated vibration generator arranged within said gripping sleeve and connected with said tartar-removing instrument to transmit vibrations thereto; media supply conduits in said gripping sleeve to conduct media therethrough; and coupling means at the end of said gripping sleeve distal from said instrument for connecting the media supply conduits with media sources; said media supply conduits including a compressed-air conduit for conducting compressed air from the coupling means to the vibration generator; the improvement comprising: said medium supply conduits further include a forward, fiber optic light conductor extending through the compressed-air conduit, and having a forward end directed towards said tartar-removing instrument; and light supplying means arranged at the end of the coupling means toward the instrument for supplying light to a rearward end of the forward light conductor.

2. Handpiece according to claim 1, wherein the light supplying means comprises an intermediate light conductor arranged in the coupling means for conducting light from a source thereof to said forward fiber optic light conductor.

3. Handpiece according to claim 1, wherein said light supplying means comprises an incandescent lamp, and a current line connected to the incandescent lamp and extending through the coupling means to conduct electric current from a source thereof to the incandescent lamp.

4. Handpiece according to claim 1, wherein the media suply conduits further include an exhaust-air conduit extending from the vibration generator for conducting compressed air therefrom.

5. Handpiece according to claim 1, wherein said medium supply conduits further include a cooling medium conduit for conducting a cooling fluid to the tartar-removing instrument.

6. Handpiece according to claim 5, wherein said light conductor forms a hollow pasageway constituting the cooling medium conduit.

7. Handpiece according to claim 5, wherein said light conductor forms a hollow passageway, and said cooling medium conduit extends through said hollow passageway.

8. Handpiece according to claim 5, wherein the cooling medium conduit includes a discharge opening for discharging the cooling fluid from the gripping sleeve, and the forward end of the light conductor is spaced from the discharge opening of the cooling medium conduit.

9. Handpiece according to claim 5, wherein the the cooling medium conduit includes a discharge opening for discharging the cooling fluid from the gripping sleeve, said discharge opening being located within the forward end of the forward light conductor.

10. Handpiece according to claim 1, wherein said coupling means is secured against rotation to said gripping sleeve.

11. Handpiece according to claim 10, wherein said coupling means is screwed to said gripping sleeve.

12. Handpiece according to claim 11, wherein said coupling means forms a threaded connection with the end of the gripping sleeve distal from the instrument, and the coupling means includes a rearwardly extending projection having external threads for connecting the coupling means to a supply hose.

13. Handpiece according to claim 1, wherein the handpiece further includes a supply hose; the coupling means is connected to an end of the supply hose towards the end of the gripping sleeve; and the coupling means includes a lock nut threadably connecting the coupling member to the end of the gripping sleeve distal from said instrument.

14. Handpiece according to claim 1, wherein said coupling means is rotatably connected with said gripping sleeve.

15. Handpiece according to claim 14, wherein said coupling means includes a quick-connect coupling freely rotatable relative to said gripping sleeve, said quick-connect coupling and the end of the gripping sleeve distal from the instrument including media transfer means operative in every rotational position of the coupling means relative to the gripping sleeve.

16. Handpiece according to claim 14, wherein said coupling means includes a guide trunnion of circular cross-section, and inserted into the end of the gripping sleeve distal from said instrument.

17. Handpiece according to claim 16, further comprising latching means for retaining the guide trunnion in a desired inserted axial position in the gripping sleeve.

18. Handpiece according to claim 16, wherein the gripping sleeve includes a plurality of fluid transfer means for conducting fluid from the coupling means to the media supply conduits independent of the annular orientation of the coupling means in the gripping sleeve, each fluid transfer means comprising: first and second, spaced sealing elements mounted on and extending around the guide trunnion, and engaging an inner wall of the gripping sleeve; and a discharge opening in the guide trunnion, between the first and second sealing elements, for discharging a fluid media from the coupling means; the guide trunnion, the first and second sealing elements, and the gripping sleeve forming an annular passageway for conducting the media from the discharge opening to a selected one of the media supply conduits.

19. Handpiece according to claim 16, wherein the light supplying means is arranged in the end of the guide trunnion toward the instrument.

20. Handpiece according to claim 1, wherein the light conductor extends coaxially within the gripping sleeve.

21. Handpiece according to claim 1, wherein the tartar-removal instrument includes a shaft extending into the gripping sleeve, and the light conductor includes a light ring extending around said shaft.

22. Handpiece according to claim 1, wherein said tartar-removing instrument is detachably connected with said vibration generator.

23. Handpiece according to claim 22, wherein a forward portion of the vibration generator forms a socket, and the tartar-removing instrument includes a rearward extension inserted into said socket.

24. Handpiece according to claim 1, wherein the vibration generator includes a resonance element, and the tartar-removing instrument is connected with said resonance element.

25. Handpiece according to claim 1, wherein the tartar-removing instrument is integrally connected with said vibration generator.

26. Handpiece according to claim 1, wherein the vibration generator extends to the end of the gripping sleeve distal from said instrument.

27. Handpiece according to claim 1, wherein a forward end of the coupling means includes a socket; and the rearward end of the light conductor extends within said socket and is held stationary by the socket relative to the light supplying means.

28. Handpiece according to claim 1, wherein the light conductor forms a hollow passageway for conducting a cooling fluid to the tartar-removing instrument; and the coupling means includes means to conduct a cooling fluid into said hollow passageway.

* * * * *